United States Patent
Jiang et al.

(10) Patent No.: US 7,179,530 B2
(45) Date of Patent: Feb. 20, 2007

(54) ANTIMICROBIAL COMPOSITE MATERIAL

(75) Inventors: Shangxin Jiang, Shanghai (CN); Isabella Luisi, Haan (DE); Sigrun Clement, Heinsberg (DE)

(73) Assignee: REBAC GmbH, Haan (DE)

( * ) Notice: Subject to any disclaimer, the term of this patent is extended or adjusted under 35 U.S.C. 154(b) by 0 days.

(21) Appl. No.: 10/495,587

(22) PCT Filed: Nov. 27, 2002

(86) PCT No.: PCT/EP02/13362

§ 371 (c)(1),
(2), (4) Date: Nov. 12, 2004

(87) PCT Pub. No.: WO03/047349

PCT Pub. Date: Jun. 12, 2003

(65) Prior Publication Data

US 2005/0084678 A1   Apr. 21, 2005

Related U.S. Application Data

(60) Provisional application No. 60/334,594, filed on Dec. 3, 2001.

(30) Foreign Application Priority Data

Mar. 5, 2002   (EP) .................................. 02004913
May 31, 2002  (EP) .................................. 02012030

(51) Int. Cl.
B32B 5/16 (2006.01)
(52) U.S. Cl. ...................... 428/403; 428/404; 428/405; 428/406; 428/407; 424/684
(58) Field of Classification Search ................ 428/403, 428/404, 405, 406, 407; 424/684
See application file for complete search history.

(56) References Cited

U.S. PATENT DOCUMENTS

| 3,325,402 A | 6/1967 | Archibald |
| 3,560,135 A | 2/1971 | Wataru et al. |
| 4,018,870 A | 4/1977 | Whittam |
| 4,098,602 A | 7/1978 | Seymour et al. |
| 4,110,504 A | 8/1978 | McIntosh et al. |
| 4,732,573 A * | 3/1988 | Hohmann et al. ............. 8/654 |
| 5,561,167 A | 10/1996 | Matsumoto et al. |
| 5,900,258 A * | 5/1999 | Engler ........................ 424/684 |

FOREIGN PATENT DOCUMENTS

| CN | 87 100231 B | 12/1987 |
| DE | 41 26 461 | 2/1993 |
| DE | 199 13 395 | 9/2000 |
| EP | 0 456 439 | 11/1991 |
| EP | 0 552 071 | 7/1993 |
| EP | 0 596 615 | 5/1994 |
| EP | 0 791 858 A | 8/1997 |
| EP | 0 887 373 | 12/1998 |
| EP | 05 10 3980 | 6/2005 |
| FR | 2793386 | 11/2000 |
| JP | 03 145410 | 6/1991 |
| JP | 04 153318 | 5/1992 |
| JP | 03 143540 | 6/2001 |
| WO | WO 86 02006 A | 4/1986 |
| WO | WO 01 48303 A | 7/2001 |

OTHER PUBLICATIONS

Wohrle et al, "Molecular sieve encapsulated organic dyes and metal chelates," Advanced Materials, VCH Verlasgesellschaft, Weinheim, DE 6(11):875-880 (1994).

* cited by examiner

*Primary Examiner*—Leszek B. Kiliman
(74) *Attorney, Agent, or Firm*—Needle & Rosenberg, P.C.

(57) ABSTRACT

The present invention relates to a composite material comprising a microparticle support, which has metallic ions and non-metallic cations grafted thereto, a process for producing said composite material and its use.

31 Claims, No Drawings

ANTIMICROBIAL COMPOSITE MATERIAL

CROSS REFERENCE TO RELATED APPLICATIONS

The present application claims priority to U.S. Provisional Application No. 60/334,594, filed Dec. 3, 2001, European Application No. 02004913.6, filed Mar. 5, 2002, European Application No. 02012030.9, filed May 31, 2002, which applications are incorporated herein fully by this reference.

BACKGROUND OF THE INVENTION

The present invention relates to a composite material comprising a microparticle support, such as a support derived from organic or inorganic particles, which has metallic ions and non-metallic cations grafted thereto, a process for producing said composite material and its use.

There are numbers of inventions and developments in non-drug, anti-bacterial materials in the last decade. Some of these materials are applied onto the surface of appliances as metal-ion coatings. Others form a sharp micro-surface that cuts bacterial cells during contact. There are also some materials grafting metallic ions (e.g. $Ag^+$, $Cu^{2+}$, or $Zn^{2+}$) onto fabric or particles to achieve anti-bacterial purposes.

There are several problems associated with the existing non-drug, anti-bacterial materials, such as high manufacturing, storage and transportation costs. The existing materials use either metallic ion or non-metallic ion grafting process which does not provide efficient anti-bacterial effects.

Accordingly, there is a need for developing a new material that is relatively low-cost in manufacture, storage, transportation and post-disposition processes, and at the same time is highly efficient for applications.

SUMMARY OF THE INVENTION

The present invention relates to
(1) a composite material ("Composite of the Invention") comprising a microparticle support having metallic ions and non-metallic cations grafted to the surface of the support;
(2) the composite material of (1) above, wherein the microparticle support consists essentially of polymeric inorganic particles, (i.e. is an inorganic microparticle support);
(3) a preferred embodiment of (1) wherein the microparticle support consists essentially of organic particles (i.e. is an organic microparticle support), preferably said particles being
(a) a copolymer of at least three monomer units, the first monomer unit being an acrylonitrile or a derivative thereof, the second monomer unit being an acrylate ester or a derivative thereof, and the third monomer unit being an ethylenically unsaturated monomer having at least one acid group, wherein in said co-polymer
(b) metallic ions are grafted to (i.e. chelated by) the cyano groups of the first monomer units and
(c) non-metallic cations are grafted to the acid groups of the third monomer unit;
(4) a method for producing the composite material according to (1) to (3) above which comprises grafting a metallic ion and/or the non-metallic cation to the surface of the organic or inorganic particles;
(5) a carpet, cloth, wiper fabric, rubber, filter, paint, polyshield, latex, glue or adhesive comprising the composite of (1) to (3) above;
(6) a polyurethane flexible foam containing the composite material of (1) to (3) above;
(7) a method for preparing the polyurethane flexible foam according to (6) above which comprises preparing a mixture out of the composite material and a polyurethane prepolymer or binder and polymerizing the mixture; and
(8) a pharmaceutical, veterinary, cosmetic or antibacterial composition comprising the composite of (1) to (3) above.

DETAILED DESCRIPTION OF THE INVENTION

In accordance with the present invention "grafting" refers to any kind of chemical interaction (e.g., covalent chemical bond, ionic interaction, non-ionic or hydrophobic interaction) between the particles and the metallic ions and non-metallic cations, respectively. With the inorganic particles of embodiment (2) "grafting" means in most cases—without being bound to any specific theory—salt formation between the negative charges on the surface of the particle and the metallic ions and the non-metallic cations. In case of embodiment (3) "grafting" metallic ions to the cyano groups of the first monomer units means that metallic ions are chelated by the cyano groups of the first monomer. By the same token, "grafting" of the non-metallic cations to the acid groups of the third monomer means that—without being bound to a specific theory—the acid groups form a salt with the non-metallic cations or covalent bond(s) between the non-metallic cations and the acid groups are formed.

According to the invention "grafting" does not mean placing the salt of a cation with a low molecular, non-polymeric organic or inorganic compound in a matrix of adhesive, e.g. in order to fix the cation to a polymer.

The wording "consists essentially of" according to the invention means a content of greater than 90%, preferably greater than 95%, and most preferably greater than 99% by weight.

In a preferred embodiment of embodiment (2) of the invention the inorganic particle is a microporous silicate, such as zeolite, iolite, and diatomite. The microporous silicate has a large amount of micropores which can adsorb silver (resulting in a silver-zeolite complex), low-cost silver series substances (ions), such as copper ions or zinc ions, and the non-metallic cations, such as cationic dyes, through cationic interchange. The resulting composite has broad-spectrum, anti-bacterial and rot resistance effects without changing the basic properties of the support. It can be used on electrical home appliance plastics, plastic films, building coatings, ceramics, rubber items, etc.

In a preferred embodiment of embodiment (3) of the present invention the first monomer unit has the formula

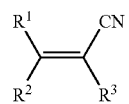

wherein $R^1$, $R^2$ and $R^3$ are independently hydrogen, a $C_{1-3}$ alkyl group or a halogenated $C_{1-3}$ alkyl group, preferably $R^1$ is hydrogen or a $C_{1-3}$ alkyl group and $R^2$ and $R^3$ are hydrogen, most preferably $R^1$, $R^2$ and $R^3$ are hydrogen. The above monomer may have E or Z configuration.

In another preferred embodiment the second monomer unit is selected from $C_{1-3}$ alkyl esters of acids selected from acrylic acid, methacrylic acid and crotonic acid, and preferably is methyl or ethyl acrylate.

In a further preferred embodiment the third monomer has the formula

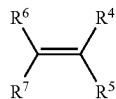

wherein $R^4$ is —$(CHR^8)_n$—$CO_2H$ or —$C(CHR^8)_nSO_3H$ (wherein $R^8$ is hydrogen, a $C_{1-3}$ alkyl group, a halogenated $C_{1-3}$ alkyl group and n is an integer from 0 to 3), $R^5$ is $CO_2H$, $CO_2R^6$, a $C_{1-3}$ alkyl group, a $C_{1-3}$ halogenated alkyl group or hydrogen, $R^6$ and $R^7$ are independently hydrogen, a $C_{1-3}$ alkyl group or a $C_{1-3}$ halogenated alkyl group, preferably $R^4$ is —$CH_2SO_3H$ or —$CH_2CO_2H$, $R^5$ is hydrogen or $CO_2H$ and $R^6$ and $R^7$ are hydrogen. The above monomer may have E or Z configuration.

In the above preferred embodiments the term "$C_{1-3}$ alkyl group" includes methyl, ethyl, n-propyl and isopropyl groups. "Halogenated $C_{1-3}$ alkyl groups" include the above $C_{1-3}$ alkyl groups, wherein 1 or more (optionally all) of the hydrogen atoms are substituted by halogen atoms such a fluorine, chlorine, bromine and iodine.

In the composite of embodiment (3) it is moreover preferred that the molar ratio of monomer units in the copolymer is 87 to 94% by weight first monomer, 5 to 10% by weight second monomer, 1 to 3% by weight third monomer.

The copolymer may be a random or block polymer or a mixture thereof. A block polymer (e.g. of the AB type or of the ABA type where the A block is composed of the first monomer and the B block is composed of the second and third monomer) is preferred.

The present invention also embraces composite materials containing both, inorganic and organic particles as microparticle support.

The metallic ions are silver series ions including, but not limited to, silver ions ($Ag^+$), copper ions ($Cu^{2+}$) and zinc ions ($Zn^{2+}$). The above ions may be used separately or as a mixture.

The non-metallic cation preferably is a nitrogen containing compound having a positive charge can be any antibacterial aliphatic or aromatic amines or ammonium compounds. Such cations include, but are not limited to, saturated or unsaturated protonated heterocycles capable of being protonated or having at least one positive charge (per se) containing at least one nitrogen atom, e.g. saturated heterocycles (such as pyrrolidine, imidazolidine, piperidine, piperazine, azepane, azepine, morpholine, DABCO (1,4-diazabicyclo[2.2.2]octane), etc.) and their derivatives (such as N-methylmorpholine, etc.), unsaturated heterocycles having at least one double bond or being heteroaromatic (such as DBN (1,5-diazabicylco[4.3.0]non-5-ene), DBU (1,8-diazabicyclo[5.4.0]undec-7-ene), imidazole, triazole, pyridine, bipyridine, pyrazine, pyrimidine, triazine, tetrazine, etc.) and their derivatives (such as substituted heterocycles (e.g. lutidine, collidine, etc.) or amino-substituted heterocycles (e.g. DMAP (4-N,N-dimethylaminopyridine), etc.), benzocondensed heteroaromatics (such as quinoline, isoquinoline, acridine, phenazine, etc.) and their derivatives, ammonium, mono-, di-, tri-alkyl-(or aryl-)amines (capable of being protonated) (such as butylamine, dibutylamine, trimethylamine, triethylamine, tripropylamine, tirbutylamine, N,N-diisopropylethylamine, benzyl-N,N-diethylamine, benzyl-N,N-dipropylamine, benzyl-N,N-dibutylamine, etc.), tetra-alkyl-(or aryl-)ammonium (such as tetraethylammonium, tetrapropylammonium, tetrabutylammonium, benzyl-N,N,N-triethylammonium, bezyl-N,N,N-tripropylammonium, benzyl-N,N,N-tributylammonium, dibenzyl-N,N-diethylammonium, etc.) and their derivatives, cationic dyes such as e.g. basic green, cationic brilliant blue, methine dyes, enamine dyes, styryl dyes, cyanine dyes, mono- and diazadimethine dyes, diphenylmethane and triphenylmethane dyes, xanthene dyes, azine dyes, azo dyes, anthraquinone dyes, phthalocyanine dyes, perinone dyes, naphthalimide dyes, quinophthalone dyes, neutrocyanine dyes, nitro dyes, etc. Particularly preferred non-metallic cations are the above-mentioned cationic dyes, in particular basic green, cationic brilliant blue, methane dyes and triptylmethane dyes, among which basic green and cationic brilliant blue are most preferred.

The composite of embodiments (1) to (3) of the invention has antibacterial properties, is mold-resistant and is in solid form and generally in a powder form. The preferred powder size is 200 to 50 mesh. The color of the composite appears different depending on the dyes added during the manufacturing process. The color can be green, yellow, blue, black, red, etc.

The "microparticle support" according to the invention is a powder having a particle size of 500 to 10 mesh, preferably 200 to 50 mesh.

It is believed that the composite of embodiments (1) to (3) has an anti-bacterial function through incorporating microsize, micro particle support of poly-microporous, non-metallic mineral (silicate) with copper or zinc ion and cationic dyes. The composite can have long-term, broad-spectrum, anti-bacterial and mold-resistant effect. The composite can be used to make anti-bacterial and mold-resistant plastics, ceramics, building coatings, rubber items, etc. It can also be used in textiles. It has a good anti-bacterial effect and broad effective spectrum. The material is non-toxic, easy to make and easy to maneuver.

One preferred embodiment of the invention is to choose silver-series substance, such as copper and zinc adsorb the silver series substance to the micro-sized support which can bind organic anti-bacterial groups, and graft organic anti-bacterial groups to the support to have a good anti-bacterial and mold-resistance effect.

For the composite material according to the invention to have antibacterial properties and to be mold-resistent it is essential that the content of the non-metallic cation is not too small, i.e. the non-metallic cation is present neither in trace amounts nor as an impurity (e.g. resulting from the manufacture of the microparticle support). According to the invention a trace amount or impurity of non-metallic cation is defined as a content of non-metallic cation being less than 0.1% by weight of the composite material and/or is defined as the non-metallic cations being present in the composite material or the microparticle support in a weight percentage ratio of non-metallic cations: metallic ions being smaller than 1.0:20.0 (i.e. the content of non-metallic cations is less than 5% by weight of the content of metallic ions).

Therefore, the content of the non-metallic cation according to the invention is defined as follows: The non-metallic cations are present in the composite material or the microparticle support in a weight percentage ratio of non-metallic cations:metallic cations not being smaller than 1.0:20.0 and/or the context of non-metallic cations is not less than 5% by weight of the content of metallic ions.

In a preferred embodiment of the invention, the weight percentage ratios among copper ion, zinc ion, porous silicate and cationic dyes are as follows: copper and zinc ions: microparticle support (e.g. porous silicate):cationic dyes are (20~40):(1.0~2.0):(0.1~0.3).

Embodiment (4) of the invention relates to a method of producing the composite of embodiments (1) to (3) which includes grafting the metallic ion and/or the non-metallic cation to the copolymer. In particular, the process for preparing the composite of embodiment (2) is as follows:
1) Preparation of a proper amount of copper or zinc salt in a ratio indicated previously;
2) Addition of 20 to 40 ml of ammoniacal liquor (concentration 26–27%) at room temperature and mixing with the salt to obtain a liquid mixture with a concentration of 1 g in 1000 to 1500 ml water;
3) Stirring the mixture for 30 to 60 minutes and putting it aside for further use;
4) Selecting a proper amount of silicate (diatomite or iolite, the particle size corresponding to a mesh value of $\geq 80$ mesh) at the ratio indicated previously;
5) Heating the silicate at 90° C. to 100° C. for 2 to 3 hours;
6) Adding the heated silicate to the mixture and stirring for 2 hours to obtain a reaction mixture;
7) Adding cationic dyes to the reaction mixture at the ratio indicated previously and stirring the cationic mixture for 30 to 60 minutes at 80° C. to 90° C.; and
8) Incubating the cationic mixture at 85±2° C. for 30 to 60 minutes, then filter-ing, washing, and baking the cationic mixture to obtain the composite as a powder.

In a preferred embodiment of the above process, during the production of the composite, a Cationic Brilliant Blue Dye is added as an additive.

In another preferred embodiment of the invention, the composite is parent particles that are composed of anti-bacterial agents, such as zinc sulfate, zinc oxide, silver nitrate, combined with polyethylene and ethylene-vinyl acetate copolymer. The process is complicated because it is confined by the fact that zeolite and water have a poor co-solubilization and a poor compatibility. The zeolite adsorption of silver-series substances is described in U.S. Pat. No. 5,900,258. China Patent No. 94118576.1 provides a method that treat the composite of plant stem from rush-family chemically and physically to firmly incorporate the micro-size silver particle onto the surface of the support. That method uses a composite of a herbaceous stem so that it is not applicable in a high-temperature resistance environment, especially in ceramics. Both use silver as the sole anti-bacterial agent, which results in high production costs.

Another preferred embodiment of the invention relates to an anti-bacterial and mold-resistance composite that is a microporous non-metallic silicate with copper ions or zinc ions on the silicate surface and in its micropores. The silicate most preferably is a diatomite or an iolite such as the one obtainable from Hongqin Aotu Company, Ltd., Jiang Su province, China.

This invention overcomes the shortcomings of existing technology as follows: Provided is a superior micro-size, physical, anti-bacterial, and mold resistance composite and its manufacturing methods. This micro-size, physical, anti-bacterial, and mold resistance composite can be used to make an anti-bacterial and mold resistant carpet, cloth, wiper, fabric, clothing, underwear, rubber, filter, paint, polyshield, latex, glue or adhesive as well as anti-bacterial and mold-resistant plastics, ceramics, building coatings, rubber items and the like. It can also be used as a constituent of fibers and textile.

Compared to the existing techniques, the present invention discloses a low production cost and simple procedure. The invention further discloses a composite that has good anti-bacterial effect, a broad anti-bacterial spectrum. The composite has a prominent killing effect on pathogenic bacteria and fungi, e.g. pyrogenic cocci (*Streptococcus* such as *Streptococcus pyrogenes*, *Streptococcus pneumoniae*, and β-hemolysing *Streptococcus*, *Staphylococcus aureus*, *Meningococcus*, *Neisseria gonorrhoea* and the like), Enterobacteriaceae (such as *Escherichia Coli*, Schmitz's *bacillus*, *Salmonella typhi*, *Salmonella paratyphi*, *Salmonella typhimurium*, *Salmonella enteritidis*, *Bacterium cholerae suis*, Morgan's *bacillus*, *Bacillus pneumonia*, *Pseudomonas aeruginosa* and the like), Pathogenic fungi (such as *Candida albicans*, *Crytococcus neoformans*, *Trichophyton rubrum*, *Trichophyton rosaceum*, *Microsporum gypseum*, thread fungus and the like), etc.

According to embodiment (3) the composite not only can be as microparticles, but may also exist in the form of fiber and fabrics, which is called "AB Antibacterial Fiber". AB is derived from both "Anti-bacterial" and the structure of molecule. A preferred embodiment of the composite material (3) is described in the following. Polyacrylonitrile (PAN) is a well-developed high-molecular material. The PAN is put in water and subjected to a reaction with cupric ion and reducing agent. During the reaction the cupric ion (group A) is grafted to the cyano group of PAN, i.e. a coordination complex is formed (the reaction is illustrated by the following Reaction Scheme (1)).

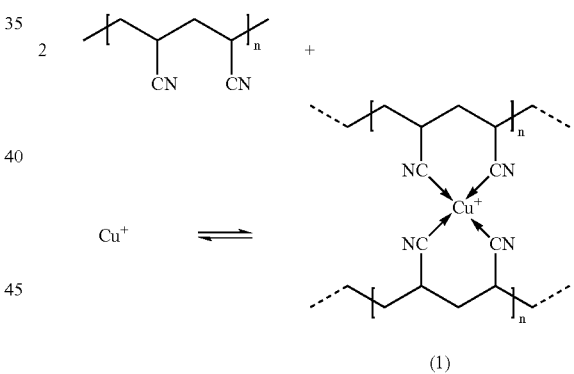

(1)

After the above reaction, the product obtained is continuously reacted with a nitrogen containing compound, such as Basic Green or another quaternary ammonium compound. The nitrogen containing compound (group B) is grafted to the third monomer of the high molecular chain. The reaction is shown in the following Reaction Scheme (2).

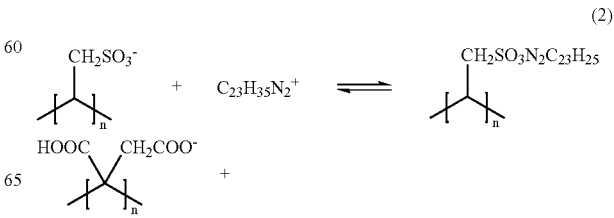

(2)

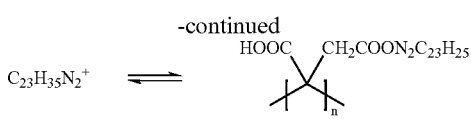

If the above reactions are combined, the final product obtained corresponds to one of the formulas depicted in Scheme (3):

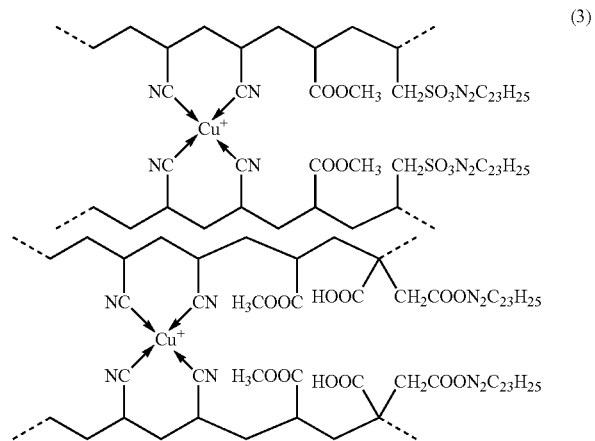

The formula in Scheme (3) can be simplified as shown in Scheme (4):

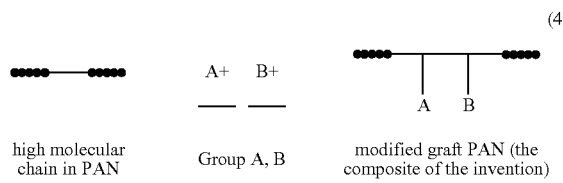

Group A: Silver-series ion containing compound
Group B: Nitrogen containing compound.

The modified graft PAN was prepared by grafting group A and group B respectively onto the high molecular chain of PAN through chemical reaction.

The above chemical reaction of a high-molecular compound is a heterogeneous reaction. Therefore, the reaction takes place on the boundary surface between two phases. Thus, the number of grafted group A and group B in said heterogeneous reaction is much less compared to a homogeneous reaction. The inventors approved with atomic absorption spectrophotometry that the modified graft PAN (the composite) contains about 0.5% of group A (such as cupric ion). We also approved with infrared spectrophotometric analysis that the graft reaction of group B truly exists. Both group A and group B on the surface have an antibacterial function; working together they give this new antibacterial material the feature of "killing bacteria with physical contact".

PAN is a petrochemical product. Based on various manufacturing procedures of different companies, the content of cyano groups and third monomer may vary a little. Accordingly, when the surface of said PAN is grafted with group A and group B, the number of group A and group B present is flexible. The deviation of the content of group A amounts to ±10% of its 0.5% by weight content.

To conclude, the composite according to the invention is an allotropic substance; it has exactly the same chemical substructure and ingredients, and the same antibacterial spectrum as the AB fiber. There is a history of more than 10 years of development of AB fiber in China. The composite according to the invention is an allotropic substance of said AB fiber. All the tests of AB fiber are applied to said composite.

The composite according to the invention is non-toxic environmental-safe material. There are no special storage and disposal requirements for the composite. The end products of the composite may require different handling based on the different materials that the composite is mixed with. In most cases, said materials are all EPA or FDA registered materials and the mixing procedures comply with EPA regulations.

In accordance with embodiments (5) and (6) the composite can be used in carpet, cloth, rubber, filter, paint, poly shield, latex, glue, adhesive, and can be incorporated into PUR flexible foams. The PUR foams obtained possess excellent antibacterial activity and can be used in hospital and sanitary applications.

The process technology for the preparation of particle foams has reached a high level of development. Therefore, in principle the scope for varying the raw materials which can be employed is very large. In addition to the classical utilization of pure PUR flexible foam scraps, textile scraps, scraps from compact plastics, microcellular polyurethanes and thermoplastic foams can also be used.

However, as in any other production, one essential precondition to the preparation of high quality products having well-defined property profiles is the use of starting materials which are as homogeneous as possible. PUR flake compound foams, such as the so-called REBOND systems, which meet these requirements, are prepared from the wide variety of production scraps obtained in the PUR block foam production and processing.

REBOND systems are prepared from selected PUR scraps. The production scraps from the preparation of block foams or molded parts are comminuted to a defined size using commercially available cutting mills. Depending on the intended product properties, flakes having a diameter of from 1 mm to 30 mm are produced.

To ensure the exactly defined property profiles of the REBOND systems, the various types of flexible foam (ether, ester, Rubex block foam and molded foam) are pretreated separately. In case extensive in-company logistics is available, it is also possible to sort according to the properties of the starting foam, such as density of foam or resistance to compression.

According to the requirements for the intended end formulation, various types of flakes are mixed in the mass ratios required, and binder systems which are particularly optimized for the individual application are added. The polyurethane prepolymers employed do wet the foam flake in an optimum manner and ensure homogeneous distribution in the matter being mixed.

The mixture prepared accordingly is employed both for the preparation of block products and in the production of molded parts. The molding process, in principle, is similar in principle to block preparation and therefore essentially can be transferred. The flakes wetted with PUR binder are charged by conveying systems into block molds having a base area of up to about 1.20 m*2.40 m, followed by two-dimensional condensing. The filling height depends on the product properties desired.

The actual reaction is effected by blowing saturated steam of 110–120° C. into the mold and is completed after 10 to 20 minutes. In rare cases, the reaction mixture is preheated with hot air. After several days of drying in an intermediate store, the demolded blocks can be processed by the conventional techniques known from PUR block foam processing. The standard assortment comprises rectangular blanks, contour blanks, profile sheets and sliced products.

The capability of employing defined and selected PUR scraps as the raw material and, in addition, a wide variety of additives for the purposeful control of additional properties in the preparation of REBOND systems offers a large number of product-specific factors for influencing product properties.

It has moreover been found that the composite of the invention can be utilized as an agent for treatment of itches, cuts and minor wounds and for the treatment of prevention and alleviation of skin diseases of humans and animals. The agent is preferably in form of a powder mixture containing the composite of the invention. This powder mixture can directly be applied to the skin (wound) or can be applied via a suitable carrier material (i.e., a cloth or fabric). The composite of the invention may also be comprised in pharmaceutical compositions suitable for oral administration.

The agent is also suitable to stabilize perishable products such as cosmetics, process aids, etc.

Finally, the composite of the invention is also suitable for preparing inactivated bacterial compositions, said compositions being suitable as pharmaceuticals, supplements etc. The obtained bacterial composition may contain the composite of the invention or may be free of it.

The followings examples illustrate the present invention, however, they are not to be construed as limiting the invention:

EXAMPLES

The chemicals listed below were purchased from Weifang No. 3 Industrial chemicals, Shanghai Pudong Chemical and Material Supply and from Guangxi Province Nanning Mineral Products. The iolite and diatomite was purchased from Hongqin Aotu (mineral stone) Company, Ltd., Jiang Su Province, China.

Example 1

Iolite as Support

Copper sulfate (0.2 g) was dissolved in water (500 ml). Ammoniacal liquor (26 to 28%; 6 ml) was added, and the mixture obtained was stirred for 30 minutes to give a blue copper liquor. Iolite (90 mesh; 10 g) was baked at 100° C. for 2 hours before it was added to the copper liquor to furnish a reaction mixture. The reaction mixture was stirred for 2 hours. Then Cationic Brilliant Blue (0.001 g) was added to the reaction mixture, which was stirred until the temperature reached 80° C. to 90° C. The mixture was kept at 85±2° C. for 30 minutes, then filtered, washed and baked to obtain a bluish green powder.

Example 2

Iolite as Support

Zinc sulfate (0.26 g) was dissolved in water (800 ml). Ammoniacal liquor (26 to 28%; 6 ml) was added, and the mixture obtained was stirred for 30 minutes. Iolite (800 mesh; 20 g) was baked at 100° C. for 2 hours before it was added to the preceding solution. The mixture obtained was stirred for 2 hours to give a reaction mixture. Cationic Brilliant Blue (0.0016 g) was added to the reaction mixture, which was stirred until the temperature reached 80° C. to 90° C. The mixture was kept at 85±2° C. for 30 minutes, filtered, washed and baked to furnish a bluish green powder.

Example 3

Diatomite as Support

Zinc sulfate (0.2 g) was dissolved in water (600 ml). Ammoniacal liquor (26 to 28%; 8 ml) was added, and the mixture obtained stirred for 30 seconds. Diatomite (90 mesh; 25 g) was baked at 100° C. for 2 hours before it was added to the mixture, which was stirred for 2 hours to give a reaction mixture. Cationic Brilliant Blue (0.0015 g) was added to the reaction mixture, which was stirred until the temperature reached 80° C. to 90° C. The reaction mixture was kept at 85±2° C. for 30 minutes, filtered, washed and baked to obtain a bluish green powder.

Example 4

Diatomite as Support

Zinc sulfate (0.3 g) was dissolved in water (500 ml). Ammoniacal liquor (26 to 28%; 8 ml) was added, and the mixture obtained stirred for 30 minutes to give a blue copper liquor. Diatomite (120 mesh; 20 g) was baked at 100° C. for 2 hours before it was added to the mixture, which was stirred for 2 hours to furnish a reaction mixture. Cationic Brilliant Blue (0.0015 g) was added to the reaction mixture, which was stirred until the temperature reached 80° C. to 90° C. The mixture was kept at 85±2° C. for 30 minutes, filtered, washed and baked to obtain a bluish green powder.

Example 5

Large Scale with Iolite as Support

1. Preparation:

The raw material came in containers of different size each time. A sample was taken from each raw material of each order. The content of copper sulfate (grade II or higher), iolite (powder, industrial grade) and basic green dye (powder, industrial grade) was determined. Each sample was divided into two packages. One package was stored for future reference, the other package was tested according to the respective manufacturer specification sheet. In case the specification was not met it was immediately reported to the supervisor. Two workers wearing gloves and a face mask weighted and packed each raw material as follows:

| | |
|---|---|
| a. Tap water | 100 liter ± 10% (one container) |
| b. Iolite powder | 100 kg ± 10% (one container) |
| c. Copper sulfate | 10 kg ± 1% (one container) |
| d. Sodium hydrogensulfate | 5 kg ± 5% (one container) |
| e. Basic green dye | 4 g ± 1% (one container). |

All containers had to be sealed for purity and to be cleaned if not being used for more than one day or being used for more than one week. All containers had to be labelled and marked. The QC sheet had to be signed for each preparation.

2. First Baking:

All working conditions had to be complied with; once the compound was mixed, it was not allowed to reuse it once it was over the indicated standby time. Iolite (100 kg) was poured into a container (container A), mixing was started, and water (1 l at a time) was added up to a total of 100 l. The mixture obtained was stirred at room temperature (10 to 25° C.) for 30 to 40 min. Any bulky deposit at the bottom of the mixture had to be avoided.

A forklift was used to place the container (container A) into an oven (oven A). The oven temperature was set to 50° C. and observed. The mixture was stirred at 30 rpm.

3. Second Baking:

Once the mixture A in oven A reached 45–55° C., the forklift was used to remove container A from oven A. Copper sulfate (10 kg) was poured into mixture A. The mixture obtained was called mixture B. Container A was put back into oven A. The temperature was set to 60° C. and observed. When a temperature of 60° C. was reached, the time was set to 30 minutes. The temperature was kept at 60° C. for 30 min. Mixture B was stirred at 20 rpm.

4. Third Baking:

Once mixture B in oven A was baked for 30 minutes, the forklift was used to remove container A from oven A. Sodium hydrogensulfate (5 kg) was poured into container A and the mixture obtained was called mixture C. Mixture C was not dry as powder at this time. Container A was put back into oven A. The temperature was set to 70° C. and observed; when this temperature was reached, the time was set to 30 min. The temperature was kept at 70° C. for 30 min. Stirring was kept at 10 rpm.

5. Fourth Baking:

Once the mixture C in oven A had been baked for 30 min, the forklift was used to remove container A from oven A. Basic green dye powder (4 g) was poured evenly into container A, and the mixture obtained was called mixture D. Mixture D was dry as powder at this stage. Container A was put into another oven (oven B). Oven A was ready immediately for use for the next batch.

The temperature was set to 80° C. and mixture D was stirred for 30 min at 5 rpm.

6. Final Baking:

Once mixture D in oven B had been baked for 30 min, the temperature of oven B was set to 95° C.

The temperature was kept at 95° C. and mixture D was stirred for another 30 min at 5 rpm.

7. Filtering:

The fork lift was used to remove container A from oven B. Oven B needed to be cooled to below 80° C. before the next run. By now the mixture in container A had an even looking color and was called compound E. Compound E was allowed to cool down until it was safe to handle.

The fork lift was used to lift container A to the conveyor line entrance. One or two workers loaded compound E onto the conveyor line channel. Compound E cooled to room temperature whilst on the conveyor line and before entering the filter. More than one filter was used in order to speed up the process. The final filter was selected according to the mesh size requirement (currently mesh 200 is required). The worker had to wear a face mask during filtering. The filtered compound was a powder called powder F.

8. Wash and Dry:

Powder F will travel into a contained section of convey line. One worker with mask and gloves will flat powder F on the bottom of the convey line. Use steam water to wash away any foreign particles and dust off the powder F. Once powder F was washed, it was stored into a shallow container (container B) for air dry. A filter mesh (200) is recommended as the cover of container B. Several container Bs will take one load of container A.

9. Packaging:

After packaging the air dried powder F was called end product G (GCM powder), from which a sample was taken. Then end product G was filled into fiber bags, which were sealed and placed in metal barrels. Once the antibacterial report showed OK, the barrels were sealed. Each barrel contained net 30 kg GCM.

10. Antibacterial Test on End Products of GCM:

For each batch (about 10 metric ton of GCM), at least two samples had to be taken to the testing room, one at the beginning of the batch and one at the end. The AATCC 1971 or 1981 method was used to test the samples. If the samples did not show an antibacterial halo (method 1971) or at least 90% antibacterial rate of 1981, the GCM of the related batch was discarded.

Example 6

Test Study an Anti-Mites Pillow on Mites-Related Allergies

Test Group:

45 volunteered patients with allergic asthmatic and allergic rhinitis disorder. Man 27, woman 18; Age 5–37, average age 39. Symptom history 2–40 years, symptom level light or medium. The patients showed a variety of allergic symptoms, such as nose itching, sternutation, rihinostegnosis (nose clog), eye itching and congestion, cough, chest asphyxia, roaring.

Material:

Anti-mites pillow, containing fibres with composite of the invention.

Test Method:

Each patient used an Elvon pillow replacing their own pillow (no towel on top of the pillowcase). One pillow per person, in a period of one month, record kept every 7 days in each symptom group.

Test Record:

| SYMPTOMS | Before | After | Effectiveness |
| --- | --- | --- | --- |
| Nose itching | 40 | 5 | 87.5% |
| Sternutation | 41 | 3 | 92.6% |
| Rhinostegnosis (nose clog) | 37 | 15 | 40.5% |
| Eye itching & congestion | 8 | 1 | 87.5% |
| Cough | 4 | 3 | 25% |
| Chest asphyxia | 2 | 0 | 100% |
| Roaring | 19 | 9 | 52.6% |

Conclusion

After 45 patients used the anti-mites for one month, the test result was as follows: The Elvon Physical Anti-Mites Pillow showed more than 80% effectiveness or improvement on symptoms like allergic asthma, allergic rhinitis, sternutation, nose itching, eye itching and congestion, chest asphyxia. Also, it helped to reduce the laryngismus caused by asthma, and then gave asthmatic patients a better sleep. The physical anti-mites pillow showed the sound and proved result of anti-mites features without any bad side effects.

Example 7

Halo Test

Test Method:

1. The composite of Example 1 was mixed with Roberts adhesive in 0.1% formula (1000 ppm), and the mixture obtained was applied to the back side of two carpet samples.
2. After drying (approx. 24 hours), a round shaped piece (1 cm in diameter) was cut from each carpet sample and placed in a cultured agar plate. Two cultured agar plates were used in this test. One was cultured with *Candida albicans*, the other one was cultured with *Bacillus subtilis*.
3. After inoculation for 18 hours at 37° C., the halo circle, which was the area free of bacteria, was measured and its size recorded.

Test Results:

| Samples | Halo Circle Measurement |
| --- | --- |
| Loop carpet in *Candida albicans* agar plate | 2–3 mm |
| Felt carpet in *Bacillus subtilis* agar plate | 3–4 mm |

SUMMARY

The composite of the invention and Robert adhesive mixture using 0.1% formula (1000 ppm) has the ability to prevent the bacteria from growing or passing through the carpet to which it is applied.

The invention claimed is:

1. A composite material comprising a microparticle support consisting essentially of polymeric organic particles and having metallic ions and non-metallic cations grafted to the surface of the support, wherein the particles are a copolymer of at least three monomer units,
   i. the first monomer unit having the formula

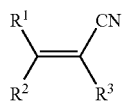

wherein $R^1$, $R^2$, and $R^3$ are independently selected from the group consisting of hydrogen, a $C_{1-3}$ alkyl group, and a halogenated $C_{1-3}$ alkyl group; said monomer having either E or Z configuration;
   ii. the second monomer unit being selected from the group consisting of $C_{1-3}$ alkyl esters of acrylic acid, methacrylic acid, and crotonic acid; and
   iii. the third monomer unit being an ethylenically unsaturated monomer having at least one acid group.

2. The composite material of claim 1, wherein the metallic ions are grafted to the cyano groups of the first monomer unit; and the non-metallic cations are grafted to the acid groups of the third monomer unit.

3. The composite material of claim 1, wherein
   i. in the first monomer unit, $R^1$ is selected from the group consisting of hydrogen and a $C_{1-3}$ alkyl group, and $R^2$ and $R^3$ are hydrogen;
   ii. the second monomer unit is selected from the group consisting of methyl acrylate and ethyl acrylate; and
   iii. the third monomer unit has the formula

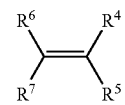

wherein
   $R^4$ is selected from the group consisting of —$(CHR^8)_n$—$CO_2H$ and —$C(CHR^8)_nSO_3H$, and wherein $R^8$ is selected from the group consisting of hydrogen, a $C_{1-3}$ alkyl group, and a halogenated $C_{1-3}$ alkyl group, and n is an integer from 0 to 3,
   $R^5$ is selected from the group consisting of $CO_2H$, $CO_2R^6$, a $C_{1-3}$ alkyl group, a $C_{1-3}$ halogenated alkyl group and hydrogen,
   $R^6$ and $R^7$ are independently selected from the group consisting of hydrogen, a $C_{1-3}$ alkyl group, and a $C_{1-3}$ halogenated alkyl group, said monomer having either E or Z configuration.

4. The composite material of claim 3, wherein
   i. in the first monomer unit, $R^1$, $R^2$ and $R^3$ are hydrogen,
   ii. the second monomer unit is selected from the group consisting of methyl acrylate and ethyl acrylate; and
   iii. in the third monomer, $R^4$ is selected from the group consisting of —$CH_2SO_3H$ and —$CH_2CO_2H$, $R^5$ selected from the group consisting of hydrogen and $CO_2H$, and $R^6$ and $R^7$ are hydrogen.

5. The composite material of claim 1, wherein the molar ratio of monomer units in the polymer is 87 to 94% by weight of the first monomer, 5 to 10% by weight of the second monomer, and 1 to 3% by weight of the third monomer.

6. The composite material of claim 1, wherein the copolymer is a block copolymer.

7. The composite material of claim 6, wherein the block copolymer is selected from the group consisting of AB type block copolymers and ABA type block copolymers, wherein the A-block is composed of the first monomer and the B-block is a random copolymer composed of the second and third monomer.

8. The composite material of claim 1, wherein the metallic ion is a silver-series ion.

9. The composite material of claim 8, wherein the metallic ion is selected from the group consisting of copper, zinc and silver.

10. The composite material of claim 1, wherein the non-metallic ion is a nitrogen containing compound having at least one positive charge.

11. The composite material of claim 10, wherein the non-metallic ion is a cationic dye.

12. The composite material of claim 11, wherein the cationic dye is selected from the group consisting of Basic Green and Cationic Brilliant Blue.

13. The composite material of claim 1, wherein the weight percentage ratio of non-metallic cation:metallic ion is not smaller than 1.0:20.0.

14. The composite material of claim 1, wherein the weight percentage ratio of the microparticle support: metallic ions: non metallic cations is (20 to 40):(1.0 to 2.0): (0.1 to 0.3).

15. The composite material of claim 1, wherein the particle diameter is from 74 to 297 μm (200 to 50 mesh).

16. A composite material comprising a microparticle support consisting essentially of polymeric organic particles and having metallic ions and non-metallic cations grafted to the surface of the support, wherein the particles are a block copolymer of at least three monomer units, i. the first monomer unit having the formula

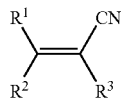

wherein $R^1$, $R^2$, and $R^3$ are hydrogen;

ii. the second monomer unit being selected from the group consisting of methyl acrylate and ethyl acrylate; and iii. the third monomer unit being an ethylenically unsaturated monomer having the formula

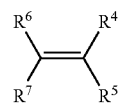

wherein $R^4$ is selected from the group consisting of $-CH_2SO_3H$ and $-CH_2CO_2$, $R^5$ is selected from the group consisting of hydrogen and $CO_2H$, and $R_6$ and $R_7$ are hydrogen.

17. The composite material of claim 16, wherein the metallic ion is selected from the group consisting of copper, zinc and silver.

18. The composite material of claim 16, wherein the non-metallic ion is a cationic dye.

19. The composite material of claim 18, wherein the cationic dye is selected from the group consisting of Basic Green and Cationic Brilliant Blue.

20. The composite material of claim 16, wherein the weight percentage ratio of non-metallic cation: metallic ion is not smaller than 1.0:20.0.

21. The composite material of claim 16, wherein the weight percentage ratio of the microparticle support: metallic ions: non metallic cations is (20 to 40):(1.0 to 2.0): (0.1 to 0.3).

22. The composite material of claim 16, wherein the particle diameter is from 74 to 297 μm (200 to 50 mesh).

23. A method for producing a composite material comprising a microparticle support consisting essentially of polymeric organic particles and having metallic ions and non-metallic cations grafted to the surface of the support, wherein the particles are a copolymer of at least three monomer units, i. the first monomer unit having the formula

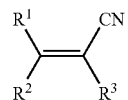

wherein $R^1$, $R^2$, and $R^3$ are independently selected from the group consisting of hydrogen, a $C_{1-3}$ alkyl group and a halogenated $C_{1-3}$ alkyl group; said monomer may have E or Z configuration;

ii. the second monomer unit being selected from the group consisting of $C_{1-3}$ alkyl esters of acrylic acid, methacrylic acid and crotonic acid; and iii. the third monomer unit being an ethylenically unsaturated monomer having at least one acid group, the method comprising grafting the metallic ion and the non-metallic cation to the surface of the organic particles.

24. The method of claim 23, wherein the copolymer is a block copolymer, and comprising the steps of:

a. preparing an amount of a metallic salt at a predetermined ratio;

b. adding 20 to 40 mL of 26 to 27% ammoniacal liquor at room temperature;

c. mixing the ammoniacal liquor with the metallic salt to obtain a liquid mixture with a concentration of 1g in 1000 to 1500 mL water;

d. stirring the mixture for 30 to 60 minutes;

e. selecting an amount of a particle at the predetermined ratio, wherein the particle size corresponds to a mesh value of $\geq 80$ mesh;

f. heating the particles at 90° C. to 100° C. for 2 to 3 hours;

g. adding the heated particles to the mixture and stirring for 2 hours to obtain a reaction mixture;

h. adding cationic dyes to the reaction mixture at the predetermined ratio to obtain a cationic mixture;

i. stirring the cationic mixture for 30 to 60 minutes at 80° C. to 90° C.;

j. incubating the cationic mixture at 85±2° C. for 30 to 60 minutes, k. filtering the cationic mixture;

l. washing the cationic mixture; and m. baking the cationic mixture to obtain the composite as a powder.

25. A carpet, cloth, wiper, fabric, rubber, filter, paint, polyshield, latex, glue or adhesive comprising the composite material of claim 1.

26. A polyurethane flexible foam comprising the composite material of claim 1.

27. A mattress or sanitary mat comprising the polyurethane flexible foam of claim 26.

28. A method for preparing the polyurethane flexible foam of claim 26, comprising preparing a mixture of the composite material and a polyurethane prepolymer or binder and polymerizing the mixture.

29. A pharmaceutical, veterinary, cosmetic or antibacterial composition comprising the composite material of claim 1.

30. A method of reducing or preventing the accumulation of bacteria and mold in an article, comprising incorporating the composite material of claim 1 into the article.

31. A method of reducing or preventing rotting of an article, comprising incorporating the composite material of claim 1 into the article.

* * * * *